US008075878B2

(12) United States Patent
Carter et al.

(10) Patent No.: US 8,075,878 B2
(45) Date of Patent: Dec. 13, 2011

(54) BROAD SPECTRUM IMMUNE AND ANTIVIRAL GENE MODULATION BY ORAL INTERFERON

(75) Inventors: William A. Carter, Spring City, PA (US); David Strayer, Byrn Mawr, PA (US)

(73) Assignee: Hemispherx Biopharma, Philadelphia, PA (US)

( * ) Notice: Subject to any disclaimer, the term of this patent is extended or adjusted under 35 U.S.C. 154(b) by 196 days.

(21) Appl. No.: 11/812,361

(22) Filed: Jun. 18, 2007

(65) Prior Publication Data

US 2008/0019943 A1   Jan. 24, 2008

Related U.S. Application Data

(63) Continuation-in-part of application No. 11/713,097, filed on Mar. 2, 2007.

(60) Provisional application No. 60/780,079, filed on Mar. 8, 2006.

(51) Int. Cl.
*A61K 38/21* (2006.01)
*A61K 38/00* (2006.01)
(52) U.S. Cl. ......... 424/85.4; 424/85.7; 514/1.5; 514/3.7
(58) Field of Classification Search .................. None
See application file for complete search history.

(56) References Cited

U.S. PATENT DOCUMENTS

| | | | |
|---|---|---|---|
| 4,950,652 A | 8/1990 | Carter et al. | |
| 5,019,382 A * | 5/1991 | Cummins, Jr. | ............... 424/85.4 |
| 5,910,304 A | 6/1999 | Cummins | |
| 6,372,218 B1 | 4/2002 | Cummins | |
| 6,509,154 B1 | 1/2003 | De Paillette | |
| 7,339,051 B2 | 3/2008 | Crooke et al. | |
| 2005/0002901 A1 | 1/2005 | Blatt | |
| 2005/0100885 A1 | 5/2005 | Crooke et al. | |
| 2005/0137154 A1 | 6/2005 | Carter et al. | |
| 2006/0024271 A1 | 2/2006 | Alibek et al. | |
| 2006/0035859 A1 | 2/2006 | Carter et al. | |
| 2007/0141080 A1 | 6/2007 | Carter et al. | |
| 2008/0019943 A1 | 1/2008 | Carter et al. | |
| 2009/0004141 A1 | 1/2009 | Carter et al. | |

FOREIGN PATENT DOCUMENTS

| | | |
|---|---|---|
| WO | 2004/013298 | 2/2004 |
| WO | 2004/092383 | 10/2004 |
| WO | 2005/009337 | 2/2005 |
| WO | 2005/019410 | 3/2005 |
| WO | 2006/082435 | 8/2006 |

OTHER PUBLICATIONS

Kuiken et al, "Pathology of Human Influenza A (H5N1) . . . ", Vet Pathol 40:304-310 (2003).

deJong et al, "Fatal Outcome of Human Influenza A (H5N1) . . . ", Nature Medicine, Advance Online Publication; 2006.
Barnard et al. "Evaluation of immunomodulators, interferons and known in vitro SARS-coV inhibitors for inhibition of SARS-coV replication in BALB/c" Antiviral Chem. Chemother. 17:275-284 (2006).
Business Wire "Ampligen® enhances the effectiveness of Tamiflu against avian influenza: Second independent preclinical study confirms dsRNA increases flu vaccine effectiveness" two pages (Sep. 2005).
Business Wire "Hemispherx Biopharma expands evaluation of Alferon N against avian flu, promising effects in bird populations to be expanded based on WHO/UN findings" two pages (Feb. 2005).
D'Agostini et al. "Combination therapy with amantadine and immunomodulators potentiates antiviral effects in influenza a virus-infected mice" Antiviral Res. 20(suppl 1):160 (abstract 217) (Apr. 1993).
Dahl et al. "In vitro inhibition of SARS virus replication by human interferons" Scand. J. Infect. Dis. 36:829-831 (Dec. 2004).
Hayden et al. "Combined interferon-$\alpha_2$, rimantadine hydrochloride, and ribavirin inhibition of influenza virus replication in vitro" Antimicrobiol. Agents Chemother, 25:53-57 (Jan. 1984).
Houston Chronicle "Anti-virus drug relieves chronic fatigue syndrome" p. 20 (Oct. 1991).
Ison & Hayden "Therapeutic options for the management of influenza" Curr. Opin. Pharm. 1:482-490 (Oct. 2001).
Pharma Business Week "Avian influenza, Ampligen enhances the effectiveness of Tamiflu against avian influenza" p. 18 (Oct. 2005).
Subbarao & Roberts "Is there an ideal animal model for SARS?" Trends Microbiol. 14:299-303 (Jul. 2006).
Tan et al. "Inhibition of SARS coronavirus infection in vitro with clinically approved antiviral drugs" Emerging infect. Dis. 10:581-586 (Apr. 2004).
World Health Organization "Management of severe acute respiratory syndrome (SARS)" two pages (Nov. 2003).
Zhao et al. "Description and clinical treatment of an early outbreak of severe acute respiratory syndrome (SARS) in Guangzhou, PR China" J. Med. Microbiol. 52:715-720 (Aug. 2003).
Int'l Search Report and Preliminary Report on Patentability for PCT/US2007/005634 (Jun. 2008).
Extended search report (EESR) for related European Patent Application, Serial No. 07867004.9 mailed Sep. 14, 2009.
Office Action issued in connection with U.S. Appl. No. 11/713,097 mailed Jul. 23, 2009. Shen, F., et al., "The immunomodulation and antiviral activity of human leucocyte interferon alpha orally administered in mice", Chinese Journal of Biochemical Pharmaceutics, 2004, vol. 25, No. 3, pp. 141-143, including ABSTRACT, published Dec. 31, 2004.

* cited by examiner

*Primary Examiner* — Christine J Saoud
*Assistant Examiner* — Jegatheesan Seharaseyon
(74) *Attorney, Agent, or Firm* — Nixon & Vanderhye P.C.

(57) ABSTRACT

An antiviral/immunomodulatory response in an animal is induced by oral administration to an infected animal, including humans, of a human α-interferon. Methods of conferring resistance or mitigating the effects of exposure to a virus including avian influenza are described.

19 Claims, No Drawings

BROAD SPECTRUM IMMUNE AND ANTIVIRAL GENE MODULATION BY ORAL INTERFERON

CROSS REFERENCE TO RELATED APPLICATION

This application is a continuation-in-part of application Ser. No. 11/713,097, filed Mar. 2, 2007 which in turn claims priority from U.S. provisional patent application Ser. No. 60/780,079 filed Mar. 8, 2006.

The present invention relates to the use of α-interferon composed of a mixture of naturally occurring α-interferons, and optionally other components for activating an immune response for combating the effects of viral infections such as avian influenza (AVI).

Viral infection of human cells results in activation of an innate immune response (the first line of defense) mediated by type 1 interferons, notably interferon-alpha (α). This normally leads to activation of an immunological "cascade", as interferon-α, acting as a type of conductor of the immune "orchestra", synchronizes the timing and relative amounts of various mediators (also termed cytokines or lymphokines) which compose the immune orchestra. If the immune orchestra conductor, specifically interferon-α, is inactivated, the orchestra members thereafter play erratically, out of sequence, etc., and the cumulative effect, rather than being beneficial and pleasant, may actually be very detrimental to the human body. Lethal acute human viruses may typically inactivate interferon-α in order to get a "foothole" within the human body Prototypic viruses behaving in this manner are avian influenza virus, SARS virus, smallpox virus, West Nile virus, and others that may kill the human host in a matter of hours, or several days (similar effects are seen in veterinary populations). Absence of interferon-α can also lead to immune dysregulation, also called "cytokine storm" which leads to overwhelming pneumonia, especially though not exclusively in AVI.

de Jong et al have found that fatal outcomes of human influenza A (H5N1) are associated with high viral load and hypercytokinemia (Nature Medicine, 2006, in press). Their studies of bases of H5N1 virulence included virological and immunological evaluations of 18 individuals with H5N1 and 8 individuals infected with human influenza virus subtypes. Influenza H5N1 infection in humans is characterized by high pharyngeal virus loads and frequent detection of viral RNA in rectum and blood. Viral RNA in blood was present only in fatal H5N1 cases and was associated with higher pharyngeal viral loads. Low peripheral blood T-lymphocyte counts and high (dysregulated) chemokine and cytokine levels were present in H5N1-infected individuals, particularly in those who died, and these correlated with pharyngeal viral loads. Genetic characterization of H5N1 viruses revealed mutations in the viral polymerase complex associated with mammalian adaptation and virulence. They report that high viral load, and the resulting intense cytokine inflammatory responses, are central to influenza H5N1 pathogenesis and recommend the focus of clinical management should be on preventing this intense cytokine response, by early diagnosis, effective antiviral treatment, and cytokine modulation.

Recent examination of the lung pathology (at post mortem) indicated that, with destruction/incapacitation of the immune orchestra conductor, interferon-α, certain mediator/"players" overreact causing immune-mediated damage to the lungs, potentially leading to death. Animal-based studies and human data (reported herein as the subject invention) indicate that the immune-inappropriate and potentially lethal, immune dysregulation, can be reregulated appropriately by very small doses of interferon-α applied briefly to the oral/buccal mucosa, either before or during early stages of otherwise overwhelming infections.

Examination of lung pathology in avian influenza not only reveals tissue injury, but also oxidative damage, pulmonary edema and hemorrhage. Interferon-α [ALFERON N used herein, a "cocktail" of 8 different molecular species of interferon from a human family of approximately 20 alpha interferons] can reverse these changes by inducing antiviral/immunomodulatory genes upon brief oral exposure. We document herein up to 385 such relevant genes which are temporarily induced by ALFERON N to perform a coordinated attack against lethal viruses and prevent cytokine overproduction leading to an inappropriate attack on host cells.

Geiss et al. (Proc Natl Acad-Sci, Aug. 6, 2002, vol 99, no 16) reported that lung epithelial pathology in pandemic influenza was due to "blocking the expression of interferon-regulated genes". Others have pointed to "profound activation of the inflammatory response", much of this being due to inappropriate expression of TNF (tumor necrosis factor), an immunoregulatory lymphokine which is effectively down-regulated by practicing the present invention.

Conspicuously, the subject invention reactivates the relevant interferon immunomodulatory pathways without significant upregulation of the inflammatory cytokines—TNF being the best studied prototypic example. This is a unique and unexpected effect of the subject invention and has wide applicability to public health in event of viral pandemics.

An objective of this invention is to provide an appropriate material and in an amount sufficient to avoid a "cytokine storm" in which the virus triggers inappropriate amounts of TNF to be produced which, in turn, causes significant excretions of fluid in the lungs and produces pneumonia-like symptoms while at the same time rendering the anti-viral properties of the interferon to be partially or completely ineffective. The invention provides a procedure for not only activating the involved genes but also refreshing other genes, an unexpected differential affect.

The α-interferon component of the therapeutic procedures herein described is preferably based upon ALFERON N INJECTION® the only approved natural, multi-species, α-interferon available in the United States. It is the first natural source, multi-species interferon and is a consistent mixture of at least seven species of α-interferon. In contrast, the other available α-interferons are single molecular species of α-interferon made in bacteria using DNA recombinant technology. These single molecular species of α-interferon also lack an important structural carbohydrate component because this glycosylation step is not performed during the bacterial process.

Unlike species of α-interferon produced by recombinant techniques, ALFERON N INJECTION® is produced by human white blood cells which are able to glycosylate the multiple α-interferon species. Reverse Phase HPLC studies show that ALFERON N INJECTION° is a consistent mixture of at least seven species of alpha interferon ($\alpha 2$, $\alpha 4$, $\alpha 7$, $\alpha 8$, $\alpha 10$, $\alpha 16$, $\alpha 17$). This natural-source interferon has unique anti-viral properties distinguishing it from genetically engineered interferons. The high purity of ALFERON N INJECTION® and its advantage as a natural mixture of seven interferon species, some of which, like species 8b, have greater antiviral activities than other species, for example, species 2b, which is the only component of Intron A. The superior antiviral activities for example in the treatment of chronic hepatitis C virus (HCV) and HIV and tolerability of ALFERON N INJECTION® compared to other available recombinant interferons, such as Intron A and Roferon A, have been reported.

ALFERON N INJECTION® is available as an injectable solution containing 5,000,000 International Units (IU) per ml.

For internal administration the α-interferon may, for example, be formulated in conventional manner for oral, nasal or buccal administration. Formulations for oral administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents.

α-interferon may be administered for therapy preferably by a suitable route including oral, nasal or topical (including transdermal, buccal and sublingual). It will be appreciated that the preferred route will vary with the condition and age of the recipient, the nature of the infection and the chosen active ingredient.

The recommended dosage of the components will depend on the clinical status of the patient and the experience of the clinician in treating similar infection. As a general guideline, dosage of ALFERON N INJECTION® utilized for systemic infections is 5 to 10 million units (sq) thrice weekly. Experience to date is with dosages above 3 IU/lb of patient body weight. Oral α-interferon (ALFERON LDO) has been administered, as a liquid solution in the range of 500-2000 IU/day and calculated on the basis of a 150 pound human this is 3.3 to 13.3 IU/lb per day.

Our experience indicates beneficial results are obtained at dosage levels of α-interferon in excess of 450 IU, that is greater than 3 IU/pound body weight. These amounts are in direct contrast to and greater than Cummins used in U.S. Pat. No. 5,910,304 of alpha interferon administration to the pharyngeal mucosa orally or as lozenge or tablet. Cummins did not anticipate differential gene modulation and the doses necessary to effectuate same.

Exposure of the oromucosa to low doses of alpha interferon has been reported to lead to biological effects in animals and humans. However, the optimal dose/schedule of low dose oral α-interferon to achieve a systemic antiviral effect is determined by the clinician. A naturally derived alpha α-interferon (ALFERON N INJECTION®) has been approved for treatment of condylomata acuminata. It is active at doses significantly lower than those used for recombinant alpha α-interferon.

EXAMPLE 1

This study was conducted to determine the prophylactic efficacy of ALFERON against Influenza H5N1 infection in cynomolgus macaques as an animal model. See Kuiken et al, Pathology of Human Influenza A (H5N1) Virus Infection in Cynomolgus Macques, Vet. Pathol. 40: 304-310 (2003).

Cynomolgus macaques (*Macaca fascicularis*) were infected with Influenza virus H5N1, demonstrated that the clinical signs in the macaques resemble those found in humans infected with the Avian Influenza H5N1 viruses, thus allowing the infection of cynomolgus macaques with Influenza H5N1 viruses to serve as a model for these infections in humans (Rimmelzwaan et al. Avian Dis. 2003; 47(3 Suppl): 931-3, Kuiken et al. Vet Pathol. 2003 May; 40(3):304-10, Rimmelzwaan et al. J. Virol. 2001 July; 75(14):6687-91).

The macaque H5N1 infection model describe above was used to determine the prophylactic efficacy of ALFERON in the cynomolgus macaque following oro-mucosal delivery of ALFERON to cynomolgus macaque following oro-mucosal delivery of ALFERON to cynomolgus macaques starting five days before intratracheal challenge with Influenza virus A/Vietnam/1194/'04 (H5N1), and followed by daily dosing for ten days at various doses.

Animals were anaesthetized before each procedure for safety and practical reasons (oro-mucosal delivery of ALFERON, and infection with Influenza virus H5N1). The experiment consisted of four groups of three animals each. Group A was treated with 10 mg/kg ALFERON, group B with 25 mg/kg ALFERON, group C with 62.5 mg/kg ALFERON and group D with placebo. There were no adverse effects observed.

Upon euthanasia at day 5 after infection macroscopic lung lesions indicated that animals from group C treated with the highest dose (62.5 mg/kg) ALFERON showed no separated dark red area(s) or diffuse dark areas on the lungs in contrast to extensive gross pathological findings in animals of the other groups. This is consistent with the microscopic findings which indicate also a lower grade of primary atypical pneumonia in both left cranial- and caudal lung lobes in animals of this group.

Thus, prophylactic treatment of macaques with oro-mucosal delivery of ALFERON demonstrated a beneficial dose dependent effect with respect to both reduced gross- and histo-pathology in treated animals.

EXAMPLE 2

Study A: asymptomatic HIV infected subjects with CD4 levels>400 were treated with 500 IU or 1,000 IU of ALFERON® in an aqueous buffered solution prepared by diluting ALFERON® for injection administered orally daily for 10 days. RNA from peripheral blood leukocytes was isolated from blood collected before, during and post-therapy using Paxgene technology for RNA isolation. A cDNA microarray analysis was utilized to identify genes which were modulated as a result of the ALFERON® oral dosing. Study B: normal healthy volunteers being studied in a similar manner.

Results indicate an induction of α-interferon related gene activity and differential gene modulation in peripheral blood leukocytes following the oral (mucosal) administration of 500 IU or 1,000 IU of a multi-species natural leukocyte α-interferon.

ALFERON® used in the study was supplied as a liquid solution packaged in sealed polypropylene lined foil pouches. Each pouch contained 1.0 ml of ALFERON® (500 IU or 1,000 IU) or placebo. Solutions were taken orally each day for 10 days. No food or water is to be taken 30 minutes prior to through 30 minutes after administration to avoid enzymatic destruction of the polypeptide mixture. Dosing and blood sampling are shown in Table 1. Dose effects are in Tables 2-4.

TABLE 1

| | | Study Day Number and Event | | | | | | | | | | | | | | | |
|---|---|---|---|---|---|---|---|---|---|---|---|---|---|---|---|---|---|
| | | Day Number | | | | | | | | | | | | | | | |
| | 0* | 1 | 2 | 3 | 4 | 5 | 6 | 7 | 8 | 9 | 10 | 11 | 12 | 13 | 14 | 15 | 16 |
| LDO Dosing | | X | X | X | X | X | X | X | X | X | X | | | | | | |
| Blood | ↑ | | ↑ | | | ↑ | | | | | ↑ | ↑ | | | | | ↑ |

TABLE 1-continued

Study Day Number and Event

| | | | | | | | | | Day Number | | | | | | | | |
|---|---|---|---|---|---|---|---|---|---|---|---|---|---|---|---|---|---|
| | 0* | 1 | 2 | 3 | 4 | 5 | 6 | 7 | 8 | 9 | 10 | 11 | 12 | 13 | 14 | 15 | 16 |
| Samples Drawn | B1 + B2 | T1 | | | T2 | | | | | | | T3 | T4 | | | | T5 |

*Day 0 = Baseline period in which two separate samples (B1 and B2) are drawn.
Goal: Compare gene expression of T1-T5 Samples to two Baseline Samples Combined (i.e. B1 + B2)

Blood samples were subjected to a cDNA Microarray Gene Analysis as follows:

Array construction. The array used in this study comprised a subset of sequence verified cDNA clones from the Research Genetics Inc. 40,000 clone set representing 950 genes containing adenylate/uridylate rich elements and 18 genes potentially involved in AU-directed mRNA decay, 855 ISGs representing an expansion of a previously described clone set containing confirmed and candidate genes stimulated by IFNs in diverse cell types, 288 genes responsive to the viral analog poly(I).poly(C), and 85 "housekeeping" genes.

Target RNA preparation. Target RNA was generated in a T7 polymerase based linear amplification reaction. Two μg total RNA and 5 pmol of t7-(dT)24 primer (5'GGCCAGT-GAATTGTAATACGACTCACTATAGGGAGGCGG-(dT)24-3' (SEQ ID NO: 1) in a total volume of 5.5 μl was incubated at 70° C. for 10 min and chilled on ice. For first strand cDNA synthesis, the annealed RNA template was incubated for 1 h at 42° C. in a 10 μl reaction containing first strand buffer (Invitrogen), 10 mM DTT, 1 U per μl anti-RNase (Ambion), 500 μM dNTPs and 2 U per μl Superscript II, (Invitrogen). Second strand was for 2 h at 16° C. in a total reaction volume of 50 μl containing first strand reaction products, second strand buffer (Invitrogen), 250 μM dNTPs, 0.06 U per μl DNA ligase (Ambion), 0.26 U per μl DNA polymerase I, (NEB) and 0.012 U per μl RNase H (Ambion) followed by the addition of 3.3 U of T4 DNA polymerase (3 U per μl; New England Biolabs) and a further 15 min incubation at 16° C. Second strand reaction products were purified by phenol:chloroform:isoamyl alcohol extraction in Phaselock microcentrifuge tubes (Eppendorf) according to manufacturer's instructions and ethanol precipitated. In vitro transcription was performed using the T7 megascript kit (Ambion) according to a modified protocol in which purified cDNA was combined with 1 μl each 10×ATP, GTP, CTP and UTP and 1 μl T7 enzyme mix in a 10 μl reaction volume and incubated for 9 h at 37° C. Amplified RNA was purified using the Rneasy RNA purification kit (Ambion).

RNA labeling. Cy3 or Cy5 labeled cDNA was prepared by indirect incorporation. Two μg of amplified RNA, 1 μl dT12-18 primer (1 μg per μl, Invitrogen), 2.6 μl random hexanucleotides (3 μg per Invitrogen) and 1 μl anti-RNAse (Ambion) were combined in a reaction volume of 15.5 μl and incubated for 10 min at 70° C. Reverse transcription was for 2 h at 42° C. in a 30 μl reaction containing annealed RNA template, first strand buffer, 500 mM each dATP, dCTP, dGTP, 300 μm dTTP, 200 μM aminoallyl-dUTP (Sigma), 10 mM DTT, 12.7 U per μl Superscript II. For template hydrolysis, 10 μl of 0.1M NaOH was added to the reverse transcription reaction and the mixture was incubated for 10 min at 70° C., allowed to cool at room temperature for 5 min and neutralized by addition of 10 μl 0.1 M HCl. cDNA was precipitated at −20° C. for 30 min after addition of 1 μl linear acrylamide (Ambion), 4 μl 3 M NaAc (pH 5.2) and 100 μl absolute ethanol than resuspended in 5 μl of 0.1M NaHC03. For dye-coupling the contents of 1 tube of NHS ester containing Cy3 or Cy5 dye (Amersham Biosciences) was dissolved in 45 μl DMSO. Five μl dye solution was mixed with the cDNA and incubated for 1 h in darkness at room temperature. Labeled cDNA was purified on a OIAQUICK PCR purification column (Qiagen) according to manufacturer's instructions. Eluted cDNA was dried under vacuum and resuspended in 30 μl of Slidehyb II hybridization buffer (Ambion). After 2 min denaturation at 95° C. the hybridization mixture was applied to the microarray slide under a coverslip. Hybridization proceeded overnight in a sealed moist chamber in a 55° C. waterbath. Post-hybridization, slides were washed successively for 5 min each in 2×SSC 0.1% SDS at 55° C., then 2×SSC at 55° C. plus a final 5 min wash in 0.2×SSC at room temperature.

Data acquisition and normalization. Data were acquired with a GenePix 4000B laser scanner and GenePix Pro 5.0 software. Raw data were imported into GeneSpring 6.0 software (Silicon Genetics) and normalized based on the distribution of all values with locally weighted linear regression (LOESS) before further analysis.

Results indicate that orally administered ALFERON® was well tolerated at the 500 and 1,000 IU/day dosage levels, cDNA microarray analysis identified 385 genes that were expressed >two fold over baseline in two or more patient samples (greater than two-fold change over baseline is statistically reliable evidence of gene modulation by the test biological drug). As shown in Tables 2, 3 and 4 an approximately four fold increase in gene expression was seen at the 1,000 IU/day dosage level compared to 500 IU/day ($p<0.0001$). Although, not an exhaustive list, Table 5 shows 25 genes that were expressed >two fold over baseline in ≧33% of patient samples. PDZ and LIN domain 5 and 2'-5' oligoadenylate synthetase-like were among the top five upregulated genes. 2'-5' oligoadenylate synthetase is an important component of the interferon intracellular antiviral pathway. Importantly, as shown in Table 6, genes related to activation of an inflammatory response such as tumor necrosis factor (TNF) related genes were actually down regulated, thus abrogating the harmful "cytokine storm".

Recent evidence shows that the virulence of influenza A including avian (H5N1) isolates correlates with the ability of the non-structural NS1 viral protein to bind to human PDZ domains and thereby abrogating the expression of antiviral genes in host cells including interferon pathways (Science xpress, 26 Jan. 2006). Thus, the finding that orally administered ALFERON® can upregulate PDZ domain expression evidences a new role, namely that ALFERON® will have an important role in abrogating the ability of influenza viruses including avian (H5N1) to evade human host defense mechanisms, resulting in a 60% death rate in infected individuals.

The orally administered ALFERON® was well-tolerated with no serious adverse events reported. Only several mild adverse events were reported, such as a transitory metallic taste in mouth or mild flatulence/bloating. There were no clinically significant changes in any standard chemical laboratory parameters and no changes in Karnofsky Performance Status (KPS).

Experiments to date indicate that a biological cocktail of natural human interferon species administered orally has systemic biological activity based on upregulation of α-interferon related genes in peripheral blood leukocytes and down-regulation of inappropriately-released cytokines, including TNF-α. Because alpha α-interferon are broad spectrum antiviral/immunomodulatory molecules, potential applications in numerous α-interferon-sensitive diseases exist, including application to respiratory infections such as avian influenza, and other systemic inflammatory diseases with inappropriate immune responses mediated in part by TNF-α or the TNF receptor family.

TABLE 2

Dose Effect: Number of Genes with Expression Increased ≧2 Fold Over Baseline in Two or More Patient Samples

| Patient # | Dose | | | | | | | | Fold Increase of Mean |
|---|---|---|---|---|---|---|---|---|---|
| | 500 IU | | | | 1,000 IU | | | | |
| | 1 | 2 | 3 | Mean | 4 | 5 | 6 | Mean | |
| Day 2 | 10 | 1 | 39 | 16.7 | 85 | 77 | 108 | 90 | 5.4 |
| Day 5 | 14 | 4 | 23 | 13.7 | 54 | 72 | 35 | 54 | 3.9 |
| Day 11 | 1 | 8 | 4 | 4.3 | 4 | 45 | 40 | 30 | 6.9 |
| Day 12 | 3 | 15 | — | 9.0 | 19 | 44 | 28 | 30 | 3.4 |
| Day 16 | — | 14 | — | 14 | 3 | 59 | 48 | 37 | 2.6 |
| Mean | 7.0 | 8.4 | 22 | 12.5 | 33 | 59 | 52 | 48 | 3.9 |

Student's t-test, p-value < 0.0001 (n = 385)

TABLE 3

Dose Effect: Number of Genes with Expression Increased ≧2 Fold Over Baseline in Three or More Patient Samples

| Patient # | Dose | | | | | | | | Fold Increase of Mean |
|---|---|---|---|---|---|---|---|---|---|
| | 500 IU | | | | 1,000 IU | | | | |
| | 1 | 2 | 3 | Mean | 4 | 5 | 6 | Mean | |
| Day 2 | 3 | 1 | 19 | 7.6 | 36 | 41 | 42 | 39.7 | 5.2 |
| Day 5 | 2 | 2 | 6 | 3.3 | 16 | 17 | 16 | 16.3 | 4.9 |
| Day 11 | 1 | 1 | 1 | 1.0 | 3 | 3 | 3 | 3.0 | 3.0 |
| Day 12 | 1 | 2 | — | 1.5 | 7 | 8 | 8 | 7.7 | 5.1 |
| Day 16 | — | 0 | — | 0 | 2 | 2 | 2 | 2.0 | >5 |
| Mean | 1.8 | 1.2 | 8.7 | 3.9 | 12.8 | 14.2 | 14.2 | 13.7 | 3.5 |

Student's t-test, p-value < 0.0001 (n = 252)

TABLE 4

Dose Effect: Number of Genes with Expression Increased ≧3 Fold Over Baseline in Two or More Patient Samples

| | Dose | | | | | | | | Fold |
|---|---|---|---|---|---|---|---|---|---|
| | 500 IU | | | | 1,000 IU | | | | Increase |
| Patient # | 1 | 2 | 3 | Mean | 4 | 5 | 6 | Mean | of Mean |
| Day 2 | 0 | 0 | 9 | 3.0 | 23 | 10 | 37 | 23.0 | 7.8 |
| Day 5 | 5 | 1 | 5 | 3.7 | 16 | 19 | 4 | 13.0 | 3.5 |
| Day 11 | 1 | 2 | 0 | 1.0 | 0 | 14 | 3 | 5.7 | 5.7 |
| Day 12 | 1 | 3 | — | 2.0 | 3 | 10 | 2 | 5.0 | 2.5 |
| Day 16 | — | 0 | — | 0.0 | 0 | 14 | 6 | 6.7 | >5 |
| Mean | 1.8 | 1.2 | 4.7 | 2.6 | 8.4 | 13.4 | 10.4 | 10.7 | 4.1 |

Student's t-test, p-value < 0.0001 (n = 69)

TABLE 5

Genes Expressed ≧ Two Fold Over Baseline in ≧ 33% of Patient Samples

| | Expression Frequency (%) | | |
|---|---|---|---|
| Identified Gene | 500 IU | 1,000 IU | Overall |
| 1 SFRS protein kinase 1 | 83 | 40 | 59 |
| 2 *Homo sapiens*, clone image: 5164031, mRNA | 17 | 87 | 56 |
| 3 PDZ and LIN domain 5 | 0 | 93 | 52 |
| 4 Interleukin 17 receptor | 0 | 93 | 52 |
| 5 2'-5' oligoadenylate synthetase-like | 33 | 67 | 52 |
| 6 Similar to KIAA0160 gene product | 0 | 87 | 48 |
| 7 N-myristoyltransferase 2 | 0 | 80 | 44 |
| 8 Proteasome (prosome, macropain) 26S subunit, ATPase, 6 | 0 | 73 | 41 |
| 9 Coagulation factor II (thrombin) receptor | 0 | 73 | 41 |
| 10 Cytochrome P450, family 51, subfamily A, polypeptide | 0 | 73 | 41 |
| 11 Interferon induced transmembrane protein 2 | 33 | 47 | 41 |
| 12 Major histocompatibility complex, class I, F | 33 | 47 | 41 |
| 13 Sarcoglycan, beta (43 kDa dystrophin-associated glycoprotein) | 0 | 73 | 41 |
| 14 Glutamate dehydrogenase 1 | 0 | 73 | 41 |
| 15 FGG | 0 | 67 | 37 |
| 16 Coagulation factor III (thromboplastin, tissue factor) | 0 | 67 | 37 |
| 17 Interferon (alpha, beta, and omega) receptor 1 | 0 | 67 | 37 |
| 18 Ribosomal protein S6 kinase, 90 KDa, polypeptide 3 | 0 | 60 | 33 |
| 19 Hemoglobin, epsilon 1 | 33 | 33 | 33 |
| 20 Acyl-coenzyme A dehydrogenase, short/branched chain | 0 | 60 | 33 |
| 21 Hypothetical protein MGC20481 | 17 | 47 | 33 |
| 22 RAB7, member RAS oncogene family | 17 | 47 | 33 |
| 23 Ribosomal protein S15a | 0 | 60 | 33 |
| 24 Glutamate dehydrogenase I | 0 | 60 | 33 |
| 25 Small nuclear RNA activating complex, polypeptide 3, 50 KDa | 25 | 40 | 33 |

TABLE 6

| Five Tumor Necrosis Factor (TNF) Related Genes with a 50% or Greater Reduction in Expression |
|---|
| 1. TNF (ligand) superfamily, member 11 |
| 2. TNF receptor superfamily, member 6b, decoy |
| 3. TNF receptor - associated factor 1 |
| 4. TNF, alpha-induced protein 6 |
| 5. TNF receptor superfamily, member 10b |

EXAMPLE 3

Reduction of atypical pneumonia in cynomolgus macaques infected with H5N1. This study was to determine the prophylactic efficacy of ALFERON LDO against Influenza H5N1 inflection in cynomologus macaques (*Macaca fascicularis*), a non-human primate animal model.

Cynomolgus macaques were treated by daily oromucosal delivery of 0.25 ml of ALFERON LDO starting 5 days before intratracheal challenge with Influenza virus A/Vietnam/1194/'04 (H5N1) and continued for another 5 days after viral challenge. The experiment consisted of four groups of three animals each. Group A was treated with 160 IU/ml ALFERON, group B with 400 IU/ml ALFERON, group C with 1,000 IU/ml ALFERON and group D with placebo. There were no adverse effects observed.

Upon euthanasia at day 5 after infection macroscopic lung lesions indicated that animals from group C treated with 1,000 IU/ml ALFERON LDO showed no adhesive fibrinous pleuritis and no separated dark red area(s) or diffuse dark areas on the lungs in contrast to animals of the other groups. This is consistent with the microscopic findings, which indicate also a lower grade of primary atypical pneumonia in both left cranial- and caudal lung lobes in animals of this group (Table 4).

All studied animals were subjected to post-mortem examinations for macroscopic and microscopic observations. All tissue samples were blinded to the pathologists during evaluation. The severity levels were graded and subjected to statistical analysis. Table 7 summarizes the results of pathological evaluations of all animals.

TABLE 7

ALFERON LDO efficacy against H5N1 in macaques demonstrating reduction in macroscopic lung lesion count and severity[1]

| Macroscopic Observation | ALFERON LDO Dose (IU/ml) | Number of animal (n) | Mean | Median | Standard Deviation | p-value[2] |
|---|---|---|---|---|---|---|
| Lung Count | 0 (placebo) | 3 | 7.3 | 8.0 | 1.2 | p < 0.01 |
| | 160 | 3 | 7.3 | 8.0 | 1.2 | |
| | 400 | 3 | 4.7 | 4.0 | 1.2 | |
| | 1,000 | 3 | 0.7 | 0.0[3] | 1.2 | |
| Lung Severity[1] | 0 (placebo) | 3 | 13.0 | 13.0 | 1.0 | p < 0.01 |
| | 160 | 3 | 16.3 | 16.0 | 1.5 | |
| | 400 | 3 | 6.7 | 6.0 | 3.1 | |
| | 1,000 | 3 | 0.7 | 0.0[3] | 1.2 | |

[1]Macroscopic abnormalities were assessed as 1 = no categorization; 2 = marginal; 3 = slight; 4 = moderate; 5 = marked; and 6 = severe.
[2]Two-sided exact Jonckheere-Terpstra test
[3]Two of three animals did not show abnormalities; hence, the median is zero.

Macroscopic examination of the lungs revealed evidence of a dose related reduction of the primary atypical pneumonia associated with infection from HPAI (p<0.01, exact Jonckheere-Terpstra test), with 2 of 3 animals in the 1,000 IU/ml group having no macroscopic evidence of infection in the lungs.

As shown in Table 8, the trend of the relationship between ALFERON LDO treatment dose and severity of the atypical pneumonia was analyzed using the exact Jonckheere-Terpstna test. The decrease in the severity of the primary atypical pneumonia was significantly related to the dose of ALFERON LDO (p<0.01).

The highest dose level of ALFERON LDO (1,000 IU/ml) showed the least severity of pneumonia with the highest severity of "moderate" occurring in only one lobe of one monkey. In contrast, the majority of the lobes examined in the monkeys that received the lower dosages of ALFERON LDO (0, 160, or 400 IU/ml) had severities of "moderate", "marked" or "severe".

TABLE 8

Significant Decrease in Primary Atypical Pneumonia (H5N1) Related to ALFERON LDO Treatment Dosage Level*

| Primary Atypical Pneumonia | | ALFERON LDO Dosage Level (IU/ml) | | | |
|---|---|---|---|---|---|
| Lobe | Severity | 0 | 160 | 400 | 1,000 |
| Cranial | Marginal | 0 | 0 | 0 | 2 |
| | Slight | 2 | 2 | 1 | 0 |
| | Moderate | 1 | 1 | 2 | 1 |

TABLE 8-continued

Significant Decrease in Primary Atypical Pneumonia (H5N1) Related to ALFERON LDO Treatment Dosage Level*

| Primary Atypical Pneumonia | | ALFERON LDO Dosage Level (IU/ml) | | | |
|---|---|---|---|---|---|
| Lobe | Severity | 0 | 160 | 400 | 1,000 |
| Caudal | Slight | 0 | 0 | 0 | 3 |
| | Moderate | 1 | 2 | 3 | 0 |
| | Marked | 1 | 1 | 0 | 0 |
| | Severe | 1 | 0 | 0 | 0 |

*p < 0.01, Two-Sided Jonckheere-Terpstra test

Viral loads in lungs of ALFERON treated animals (groups A, B and C) did not show the tendency of being lower than the viral loads in lungs of Placebo treated animals.

These data show 10 days of prophylactic and therapeutic treatment of macaques with oromucosal delivered ALFERON LDO at a dose of 1,000 IU/ml appears to mitigate the development of pneumonia despite the continuing presence of the influenza virus. ALFERON LDO demonstrates a beneficial dose dependent effect with reduced gross- and histopathological findings related to the primary atypical pneumonia in cynomolgus macaques infected with H5N1/avian influenza.

The relationship of ALFERON LDO doses between macaque and human is shown in Table 9. The current efficacious dose of 1,000 IU/ml in macaques would translate to a dose of 4,725 IU in adult humans with an average body weight of 75 kg.

TABLE 9

ALFERON LDO doses between macaques and humans
ALFERON LDO Dose in Macaques

| IU/kg | IU/ml |
|---|---|
| 10 | 160 |
| 25 | 400 |
| 63 | 1,000 |

EXAMPLE 4

Up-Regulation of Antiviral and Immune Response Genes

Phase 2 clinical study designed to investigate the activity and safety of ALFERON LDO in HIV positive subjects with early stage disease is being conducted. The endpoints of the study include an increase or up-regulation of expression of genes known to be mediators of the natural immune response using gene chip technology. Patients are randomized to a particular dose ranging from 500 IU/ml to 2000 IU/ml, and receive one ml of ALFERON LDO daily for 10 days. Blood samples are drawn for 2 separate baseline timepoints, and then on days 2, 5, 11, and 16. For each timepoint, Amplified RNA from the sample is labeled and used as a probe to evaluate the level of expression on focused microarray slides containing 3,800 relevant interferon responsive genes.

Gene expression analysis shows induction of multiple antiviral genes consistently at the 1000 IU/ml dose. Table 10 summarizes the consistent changes in gene activity. Classical interferon induced genes are upregulated, such as MHC class I proteins and interferon receptors. Most notably, a particular gene, PDZ-LIM5 is upregulated. A large-scale sequence analysis on avian isolates from the extensive St. Jude Influenza Repository identified a PDZ ligand domain in the non-structural NS1 protein as a likely virulence factor. The NS1 protein of influenza A has been implicated in the evasion of the host defense mechanisms by inhibition of the IFN antiviral system. The induction of a PDZ decoy may offer protection to PDZ-sensitive biological processes. Influenza NS1 proteins can reduce interferon production in infected cells by binding to dsRNA generated during viral replication. In addition, pandemic influenza NS1 proteins, but not seasonal NS1 proteins, also bind to PDZ proteins involved in cytoplasmic scaffolding and viral signaling. The PDZ-LIM5 upregulation may further help override the inhibitory activity of the pandemic NS1 proteins and thereby lessen the lethality of H5N1. Similarly, up-regulated levels of 2'-5'-AS and similar genes would provide inhibition of protein synthesis in the newly infected cell.

TABLE 10

Genes Expressed ≧ Two Fold over Baseline in over 35% of ALFERON LDO Treated Patient Samples

| | Expression Frequency | |
|---|---|---|
| Identified Gene (>2× increase) | 500 IU/ml | 1,000 IU/ml |
| Antiviral Genes | | |
| 1 PDZ and LIM domain 5 | 0 | 93 |
| 2 2'-5' oligoadenylate synthetase (OAS)-like | 33 | 67 |
| 3 Interferon induced transmembrane protein 2 | 33 | 47 |
| 4 Interferon R (alpha, beta, omega) receptor 1 | 0 | 67 |
| Immunological Response Genes | | |
| 1 Interleukin 17 receptor | 0 | 93 |
| 2 Proteasome (macropain) 26S subunit ATPase 6 | 0 | 73 |
| 3 Major histocompatibility complex class 1 F | 33 | 47 |

The above results demonstrate that ALFERON LDO, particularly at 1000 U dose, is associated with upregulation of crucially needed antiviral genes to thwart influenza.

EXAMPLE 5

Down-Regulation of TNF Superfamily Genes: Treatment for Cytokine Storm

The HIV patients enrolled in the study described in Example 4 were also analysed for the expression of tumor necrosis factor (TNF) superfamily genes. Table 11 shows the expression of five TNF related genes in 6 HIV patients, 3 treated with 500 IU/ml and 3 treated with 1000 IU/ml. At 1000 IU/ml dose group, it is prominent that TNF related gene expressions were consistently down-regulated with a 50% or greater reduction beginning at day 2.

TABLE 11

Five Tumor Necrosis Factor (TNF) Related Genes with a 50% or Greater Reduction in Expression in HIV Patients Treated with ALFERON LDO

| | Days TNF Genes were Down-Regulated | | | | | |
|---|---|---|---|---|---|---|
| | 500 IU/day | | | 1000 IU/day | | |
| | Patient Number | | | | | |
| TNF Superfamily Genes | 1 | 2 | 3 | 4 | 5 | 6 |
| TNF ligand superfamily, member 11 | | | | | Day 5, 16 | Day 2, 12 |
| TNF receptor superfamily, member 6b, decoy | | | | Day 2, 5, 16 | | |
| TNF receptor associated factor 1 | Day 12 | | | Day 16 | Day 2 | |
| TNF alpha-induced protein 6 | | | | Day 11 | Day 5, 11 | |
| TNF receptor superfamily, member 10b | | | | | Day 5 | Day 2 |
| Total gene down regulated | 1 | 0 | 1 | 6 | 4 | 3 |

Influenza viral infection triggers an acute expression of cytokines (cytokine storm); some of them are associated with inflammation, which may contribute to the severity of the diseases process. The down regulation of the TNF superfamily genes observed in patients may improve the secondary immune dysregulation from influenza infection.

We claim:

1. A method of mitigating the effects of or conferring resistance to a susceptible viral infection, wherein said viral infection is any pathogen that replicates by a mechanism similar to human or avian influenza virus, comprising, prior to exposure to a virus or shortly after exposure to the virus, but prior to the development of symptoms, orally or nasally administering to an animal α-interferon in an amount of at least 6.6 IU per pound of the animal's body weight so that the effects of the viral infection are mitigated or the resistance is conferred.

2. The method of claim 1 wherein the viral infection is avian influenza.

3. The method of claim 1 wherein the α-interferon is administered orally or nasally to abrogate the "cytokine burst" leading to inappropriate immune response.

4. The method of claim 1 wherein said animal is a human.

5. A method of conferring resistance to or mitigating the effects of an infectious, avian influenza virus; the method comprising: prior to exposure to the virus or shortly after exposure to the virus, respectively, and prior to development of symptoms from infection by the virus, orally or nasally administering multiple, glycosylated α-interferon species to a human patient in an amount of at least 6.6 IU per pound of the patient's body weight so that the resistance is conferred or the effects are mitigated.

6. The method of claim 5 wherein the α-interferon species were purified as a mixture of at least seven species of α-interferon produced by human white blood cells.

7. The method of claim 6 wherein the α-interferon species are orally administered in an amount in the range of 1,000-10,000 IU per day.

8. The method of claim 6 wherein the α-interferon species are orally administered in an amount of at least 6.6 IU per pound of the patient's body weight.

9. The method of claim 8 wherein the α-interferon species are orally administered in an amount in the range of 1,000-10,000 IU per day.

10. The method of claim 6 wherein the α-interferon species are nasally administered in an amount of at least 6.6 IU per pound of the patient's body weight.

11. The method of claim 10 wherein the α-interferon species are nasally administered in an amount in the range of 1,000-10,000 IU per day.

12. The method of claim 6 wherein the α-interferon species are nasally administered in an amount in the range of 1,000-10,000 IU per day.

13. The method of claim 5 wherein the α-interferon species are orally administered in an amount of at least 6.6 IU per pound of the patient's body weight.

14. The method of claim 13 wherein the α-interferon species are orally administered in an amount in the range of 1,000-10,000 IU per day.

15. The method of claim 5 wherein the α-interferon species are orally administered in an amount in the range of 1,000-10,000 IU per day.

16. The method of claim 5 wherein the α-interferon species are nasally administered in an amount of at least 6.6 IU per pound of the patient's body weight.

17. The method of claim 5 wherein the α-interferon species are nasally administered in an amount in the range of 1,000-10,000 IU per day.

18. The method of claim 17 wherein the α-interferon species are nasally administered in an amount in the range of 1,000-10,000 IU per day.

19. The method of claim 5 wherein a "cytokine burst" leading to inappropriate immune response is abrogated.

* * * * *

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggccagtgaa ttgtaatacg actcactata gggaggcggt ttttttttt ttttttttt    60 ttt                                                                63
```